United States Patent
Yang et al.

(10) Patent No.: US 7,332,349 B2
(45) Date of Patent: Feb. 19, 2008

(54) DETECTION OF CELL MEMBRANE-ASSOCIATED PROTEINS USING MEMBRANE FRAGMENTS DISPLAYED ON ENCODED MICROPARTICLE ARRAYS

(76) Inventors: Jiacheng Yang, 3 Hawley Rd., Hillsboro, NJ (US) 08844; Enqing Tan, 3 Jared Blvd., Kendall Park, NJ (US) 08824

(*) Notice: Subject to any disclaimer, the term of this patent is extended or adjusted under 35 U.S.C. 154(b) by 403 days.

(21) Appl. No.: 10/891,911

(22) Filed: Jul. 15, 2004

(65) Prior Publication Data
US 2005/0059095 A1 Mar. 17, 2005

Related U.S. Application Data

(60) Provisional application No. 60/487,452, filed on Jul. 15, 2003.

(51) Int. Cl.
*G01N 33/564* (2006.01)
(52) U.S. Cl. .................... 436/507; 435/4; 435/7.1; 435/7.23; 435/7.24; 435/7.92; 435/7.94; 435/173.4; 435/287.2; 435/288.3; 435/372.2; 435/372.3; 435/971; 436/503; 436/518; 436/523; 436/524; 436/528; 436/546; 436/44
(58) Field of Classification Search .............. 435/2, 435/4, 7.1, 7.23, 7.24, 287.2, 971, 7.92, 7.94, 435/173.4, 288.3, 372.2, 372.3, 973; 436/507, 436/512, 513, 518, 523, 524, 528, 546, 10, 436/17, 46, 164, 165, 175, 177, 503, 44, 436/172

See application file for complete search history.

(56) References Cited

U.S. PATENT DOCUMENTS 5,948,627 A * 9/1999 Lee et al. ................. 435/7.24
6,251,691 B1 * 6/2001 Seul ........................ 436/534

OTHER PUBLICATIONS

Sumitran-Karuppan et al., The use of magnetic beads coated with soluble HLA class I or class II proteins in antibody screening and for specificity for determination of donor-reactive antibodies, Transplantation 61 (10): 1539-1545 (May 27, 1996).*

Zaer, Farid, et al. "Antibody Screening by Enzyme-Linked Immunosorbent Assay Using Pooled Soluble HLA in Renal Transplant Candidates". *Transplantation*. Jan. 15, 1997: 48-51. vol. 63, No. 1.

Wilson, Mark R., et al. "A New Microsphere-based Immonofluorescence Assay for Antibodies to Membrane-associated Antigens." *Journal of Immunological Methods*. 1988:231-237. vol. 107.

Scillian, James J., et al. "Early Detection of Antibodies Against rDNA-Produced HIV Proteins With a Flow Cytometric Assay". *Blood*. May 15, 1989: 2041-2048. vol. 73, No. 7.

(Continued)

Primary Examiner—Gailene R. Gabel
(74) Attorney, Agent, or Firm—Eric P. Mirabel

(57) ABSTRACT

Disclosed are methods relating to cell membrane fragments associated with microbeads, so that the characteristics of the cells the fragments originated from can be determined. The fragments can be oriented with what was the outer surface of the cell membrane facing outwardly, so that the antigens associated with the membrane can be contacted with ligands (including antibodies) to antigens in the membranes which would be accessible to antibodies in vivo. The system is useful, inter alia, for detection of panel reactive antibodies in donor serum, as well as detection of other cell membrane antigens; or quantitation of particular cell membrane antigens.

6 Claims, 5 Drawing Sheets

OTHER PUBLICATIONS

Frengen, Jomar, et al. "Demonstration and Minimization of Serum Interference in Flow Cytometric Two-Site Immunoassays". *Clinical Chemistry*. 1994: 420-425. vol. 40, No. 3.

Shoyer, Terrie W., et al. "A Rapid Flow Cytometry Assay for HLA Antibody Detection Using A Pooled Cell Panel Covering 14 Serological Crossreacting Groups". *Transplantation*. Feb. 27, 1995: 626-630. vol. 59, No. 4.

Sumitran-Karuppan, Suchitra, et al. "The Use of Magnetic Beads Coated With Soluble HLA Class I or Class II Proteins in Antibody Screening and for Specificity Determination of Donor-Reactive Antibodies." *Transplantation*. May 27, 1996: 1539-1545. vol. 61, No. 10.

* cited by examiner

DETECTION OF CELL MEMBRANE-ASSOCIATED PROTEINS USING MEMBRANE FRAGMENTS DISPLAYED ON ENCODED MICROPARTICLE ARRAYS

RELATED APPLICATIONS

Priority is claimed to U.S. Provisional Application No. 60/487,452, filed Jul. 15, 2003.

BACKGROUND

Determining the type and relative proportion of an individuals' cell surface or membrane-associated proteins is medically useful because over-expression, under-expression or complete lack of certain receptors or transmembrane channels frequently is indicative of disease or state of disease. If certain receptors are over-expressed, certain drugs may cause adverse events or toxicity. Conversely, if certain receptors are under-expressed or completely absent, certain drugs may not be effective, and signal transduction may not occur.

Human leukocyte antigens (HLA) represent a class of cell surface proteins (also referred to herein as transplantation antigens), whose great variability from one individual to another forms the molecular basis for the immune system's ability to distinguish "self" from "non-self" cells and tissues. Individuals sensitized to HLA, for example in the course of pregnancy, or as a result of blood transfusion or organ transplantation, develop allo-antibodies, also referred to as "panel-active antibodies" (PRA). The presence in a prospective transplant recipient of antibodies against donor HLA alleles, also known as a "donor-specific cross-match," is predictive of a high risk of graft rejection. It is standard practice in transplantation medicine to test all potential recipients against a panel of HLA antigens selected to represent a human population and to determine the percentage of HLA alleles against which the recipient's serum is reactive. In this "panel-reactive antibody" (PRA) testing, serum reactivity against a high percentage of HLA alleles present in a normal human population is predictive of a high risk of graft rejection. To minimize the risk of an adverse immune response leading to rejection of grafts of tissue, organ, bone marrow or transfused blood, recipients are tested to ascertain their spectrum of allo-antibodies directed against the donor's HLA spectrum (or, in the case of blood transfusion, blood group antigens).

Methods known in the art for HLA testing include the complement-dependant lymphocytotoxicity test in which serum from a recipient is incubated with donor or panel lymphocytes (such lymphocytes being representative of a spectrum of HLA in the general population) followed by incubation with complement. The level of cytotoxicity is then estimated by discriminating between dead and viable cells using a dye. This method is labor intensive, requires viable cells, may be nonspecific and requires a subjective evaluation of the cells.

Pouletty et al., U.S. Pat. No. 5,223,397, disclose methods for testing HLA compatibility between a donor and a recipient comprising the steps of adding blood from the donor to a substrate having anti-HLA antibodies bound thereto, and incubating for sufficient time for soluble HLA antigens present in the blood to bind to the antibodies or ligand. Blood from the recipient is then added to the solid substrate, whereby any antibody specific for any HLA antigens bound to the solid substrate may become bound. The detection of an absence of antibodies from the recipient's blood to the HLA antigen is indicative of a suitable cross-match.

Zaer et al., "Antibody screening by enzyme-linked immunosorbent assay using pooled soluble HLA in renal transplant candidates," Transplantation 63: 48-51 (1997) discloses use of an ELISA using HLA class I molecules purified from pooled platelets to detect anti-HLA antibodies. In patients found to not be sensitized, the incidence of false-positive results was less for ELISA testing than for panel studies. In patients who were highly sensitized, both tests performed equally well, whereas discordant results were registered mainly in cases of mild sensitization. In such cases, the incidence of false-negative results was higher for ELISA testing than for panel studies.

Flow cytometry assay methods have been used for analysis of membrane antigens and antibodies thereto. Wilson et al., "A new microsphere-based immunofluorescence assay for antibodies to membrane-associated antigens," J. Immunol. Methods 107: 231-237 (1988) disclose the use of polyacrylamide microspheres coupled with cell membrane proteins in immunofluorescence assays for antibodies to membrane-associated antigens. The method is said to make possible the rapid flow cytometric analysis of plasma membrane antigens from cell populations that would otherwise be unsuitable for use in flow cytometry.

Scillian et al., "Early detection of antibodies against rDNA-produced HIV proteins with a flow cytometric assay," Blood 73: 2041-2048 (1989) disclose the use of immunoreactive beads in flow cytometric assays for detection of antibodies to HIV. Frengen et al., Clin. Chem. 40/3: 420-425 (1993) disclose the use of flow cytometry for particle-based immunoassays of alpha-fetoprotein (AFP). This reference further reports the ability of serum factors to cross-link labeled mouse monoclonal antibodies of irrelevant specificity to different particle types coated with various immunoglobulins.

Flow cytometry methods using lymphocytes encounter difficulties arising from the activity of auto-antibodies, as reported in Shroyer et al., Transplantation 59:626-630. Moreover, when using flow cytometry with lymphocytes, use of ten or more different lymphocytes tends to produce confusing signals. As a consequence, studies using lymphocytes have been limited to presenting a small panel of HLA antigens that do not adequately reflect the distribution of HLA antigens in a normal human population.

Sumitran-Karuppan et al., "The use of magnetic beads coated with soluble HLA class I or class II proteins in antibody screening and for specificity," Transplantation 61: 1539-1545 (1996) disclose the use of magnetic beads which use an anti-HLA capture antibody to immobilize a variety of soluble HLA antigens pooled from 80 to 100 individuals on each bead. The beads can then be directly added to patient serum for efficient absorption of HLA antibodies. The reference discloses visualization of antibody binding to the antigen-coated beads using flow cytometry and suggests that this will allow testing for antibody specificity for cross-matching purposes and for the screening of panel-reactive antibodies. The methods of Sumitran-Karuppan are limited, however, because the pooling of antigens causes sensitivity to certain rare HLA antigens. Moreover, the method is not capable of quantifying the relative amounts of PRA.

Flow cytometry analysis is performed as a separate analytical step after completion of the assay for profiling of allo-antibodies. What is needed is an analysis that integrates the assay with instant subsequent read-out, thereby facilitating greater convenience, ease-of-use and high sample throughput, hence enhancing productivity. The method should provide a universal platfonm for the quantitative analysis of proteins, nucleic acids and cells.

SUMMARY

Disclosed is a parallel format of detecting the presence of multiple cell-surface, transmembrane or other cell-membrane-associated proteins, including receptors such as G-protein-coupled receptors or other receptors mediating signal transduction, including ion channels, and further including cell surface antigens, including HLA. The parallel format of analysis comprises the preparation of arrays of encoded microparticles, wherein these microparticles are decorated with fragments of cell membranes derived from different sources. In a parallel format of analysis, arrays of bead-displayed membrane fragments, assembled on a planar substrate such as a silicon chip, are permitted to react with cognate ligands following which a detection step reveals the formation of receptor-ligand complexes on individual beads within the array. Preferably, both the bead encoding tags as well as the assay signals produced in the secondary labeling step are detected by fluorescence microscopy, and it is possible to detect both in a single step The Random Encoded Array Detection (READ) format described herein to form arrays of membrane fragments permits integration of assay and essentially instantaneous read-out, thereby facilitating greater convenience, ease-of-use and sample throughput, and hence enhancing productivity. A further advantage arises from assay miniaturization and attendant reduction in reagent consumption. The present invention also discloses the combination of allo-antibody profiling with auto-antibody profiling as well as "cross-matching" by means of bead-displayed anti-B-cell specific and anti-T-cell specific monoclonal antibodies.

In one aspect, the invention provides for the simultaneous determination of the reactivity of the endogenous antibodies from a potential graft recipient with a panel of human leukocyte antigens ("HLA") representative of HLAs present in the potential donor population.

For multiplexed profiling of allo-antibodies, membrane fragments are derived from several cells, each presenting a specific set of class I and class II HLA, and fragments affixed to encoded beads within a planar array are contacted with patient sera under conditions permitting the capture of circulating allo-antibodies to membrane-embedded HLA. For detection, antigen-antibody complexes on individual beads are labeled in a secondary step by standard methods, such as using a labeled secondary antibody which targets the bound antibody of the antigen-antibody complex. To construct a membrane fragment array that is representative of the redundancy of antigens in the general population, several sets of cell lines presenting overlapping sets of typically four to six HLA, are processed to produce membrane fragments which are then affixed to encoded beads by the methods herein.

A preferred orientation of membrane fragments is such that the extracellular portions face the analyte solution to enhance the accessibility of extracellular recognition sites and epitopes. To this end, micropaticles ("beads") are first functionalized as described herein by covalent attachment of monoclonal antibodies or fragments thereof directed against domains of certain transmembrane proteins located on the inner side of the cell membrane, or against phosphatidylserine or phosphatidylethanolamine, which are phospholipids which are more prevalent on the intracellular side of cellular membranes than on the extracellular side. Membrane fragments will be captured by such functionalized beads, in most cases in a preferred orientation, due to the relative distribution of phosphatidylserine and phosphatidylethanolamine on the respective surfaces. Maintaining this orientation is particularly desirable when one is targeting receptors or antigens whose recognition sites or epitopes reside or are associated with the outer cell surface, as in the case of class I and class II HLA.

To determine the percentage of reactive antibodies, membrane fragment arrays displaying a representative spectrum of antigens are contacted with patient sera. Following completion of the labeling step, the percentage of bead types within the array scoring positive is determined. In contrast to conventional methods of using allo-antibody typing trays which require placement of multiple aliquots of patient serum into each of multiple wells which contain cells from different individual cell lines, the READ™ format used herein completes the entire analysis on a single small aliquot of serum by performing a fully "multiplexed" analysis in a single reaction using a random encoded array of membrane fragments. To increase the accuracy of the assay, antibodies purified from human serum could be used in the assay. The array optionally may contain additional molecular receptors of interest, such as a subarray of encoded bead-displayed auto-antigens. The entire array is small in size. In contrast to flow cytometric methods of analysis of the prior art, no separate step of analysis is required.

In another aspect, the existence of cell-associated antigens in a given serum sample can be determined in a multiplexed manner. Specifically, this method of analysis relates to a multiplexed "panning" format of cross-matching in which random encoded arrays of microparticles are used to display antibodies directed against B-cell specific and T-cell specific cell surface antigens. More generally, where only certain types of cells in the serum express (or express increased amounts of) certain cell-associated antigens—for example, antigen presenting cells will present certain antigens on their cell surface as part of the immune response—the sample is placed in contact with a random encoded array of microparticles displaying antibodies directed against the cell-surface antigens of interest.

BRIEF DESCRIPTION OF THE DRAWINGS

FIG. 2A depicts the class II-specific detection of HLA antigens in a PBL sample using human polyclonal serum.

3A depicts the class I-specific detection of FLA antigens in a spleen sample using human polyclonal serum.

Figure 1:
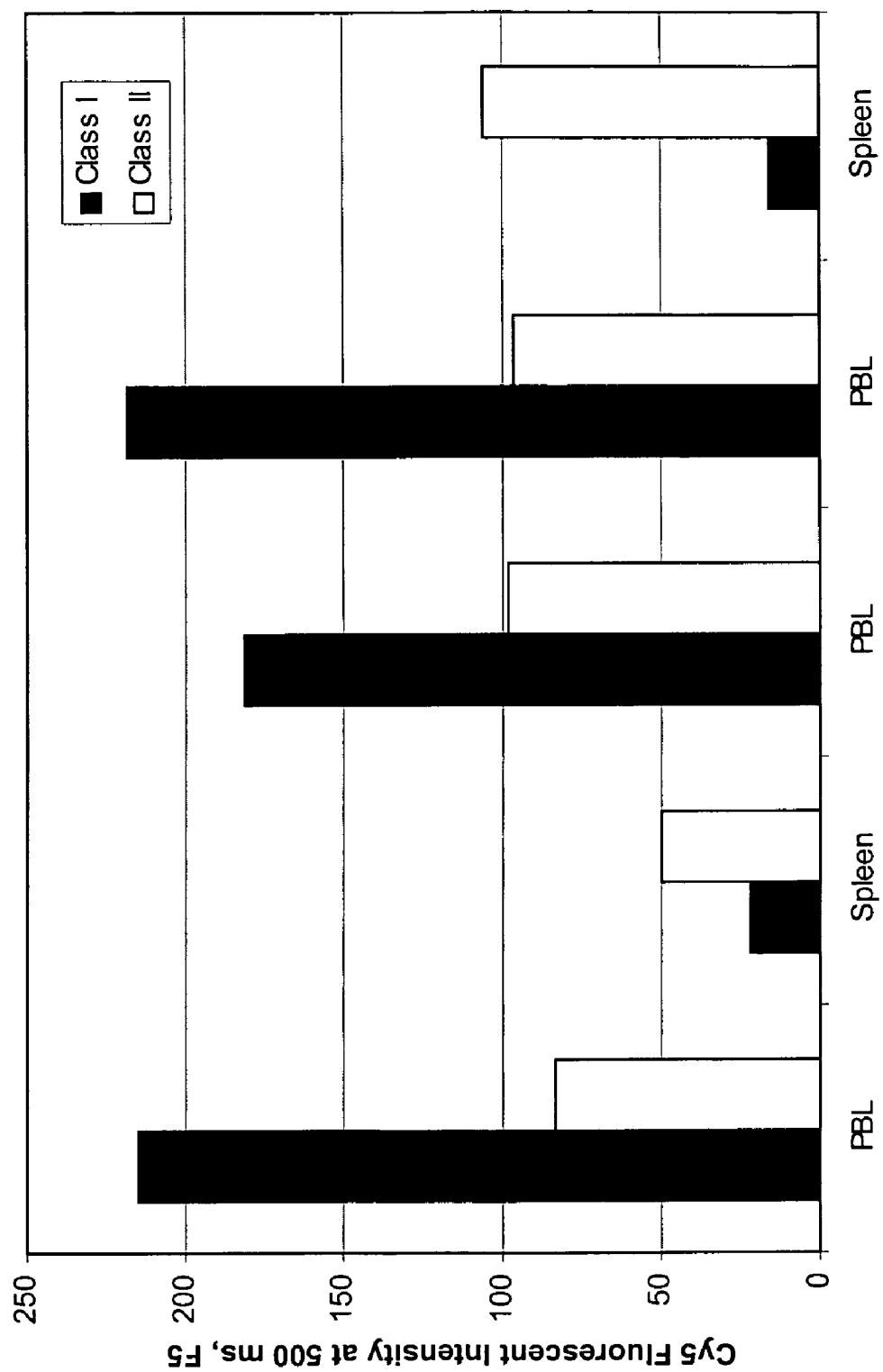
FIG. 1 depicts the results of an assay of membrane fragments in a microparticle array format showing the abundance of Class I and Class II HLA presented on cells purified from blood (PBLs) and spleen.
Figure 2A:
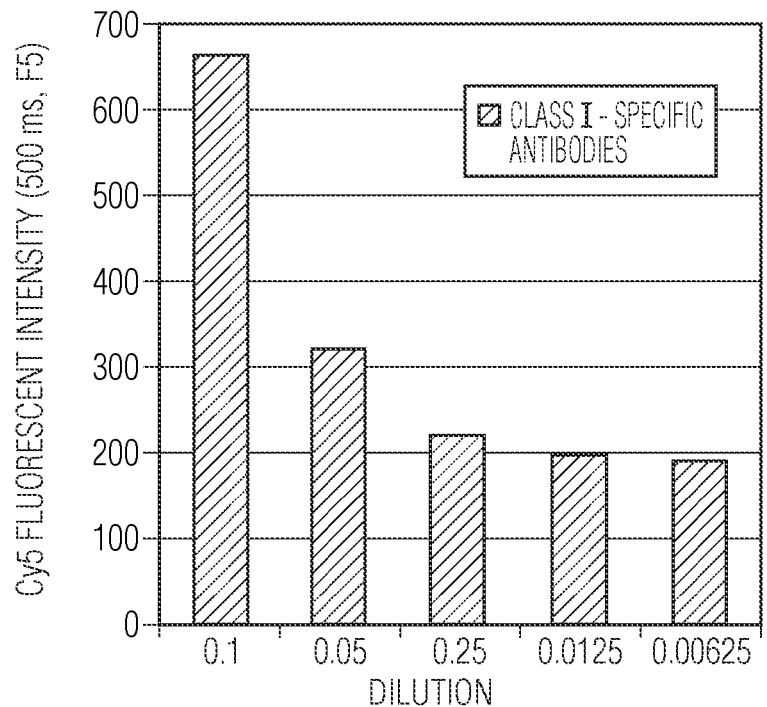
FIG. 2A depicts the class I-specific detection of HLA antigens in a PBL sample using human polyclonal serum.
Figure 2B:
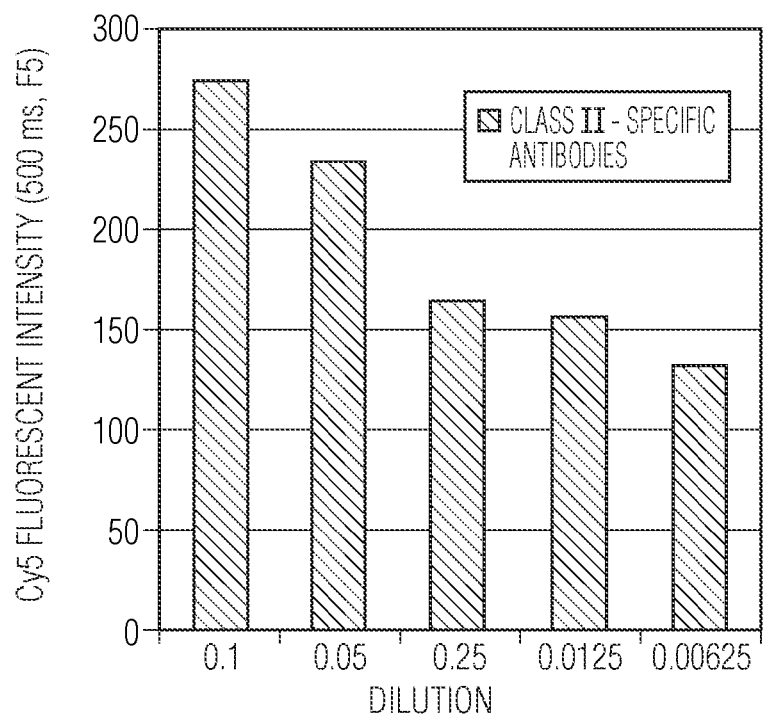
Figure 3A:
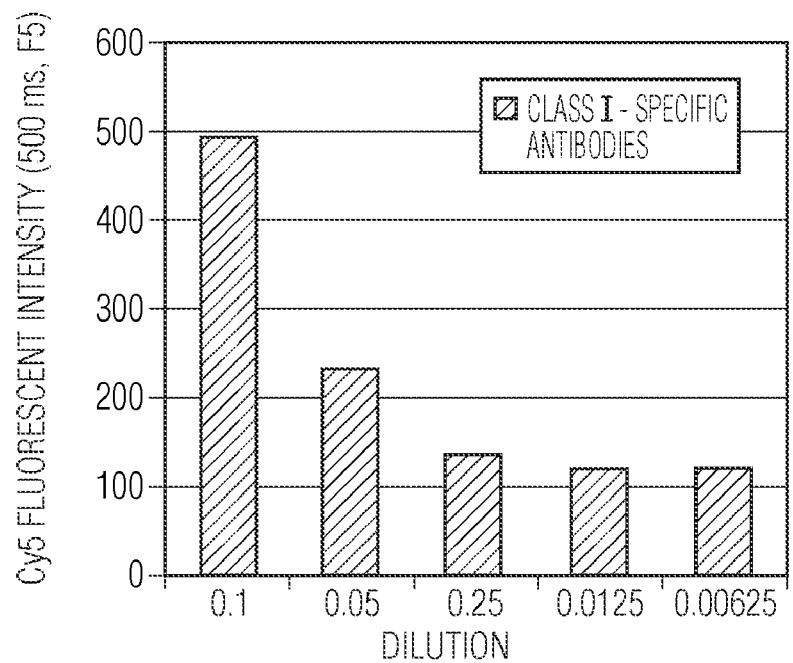
Figure 3B:
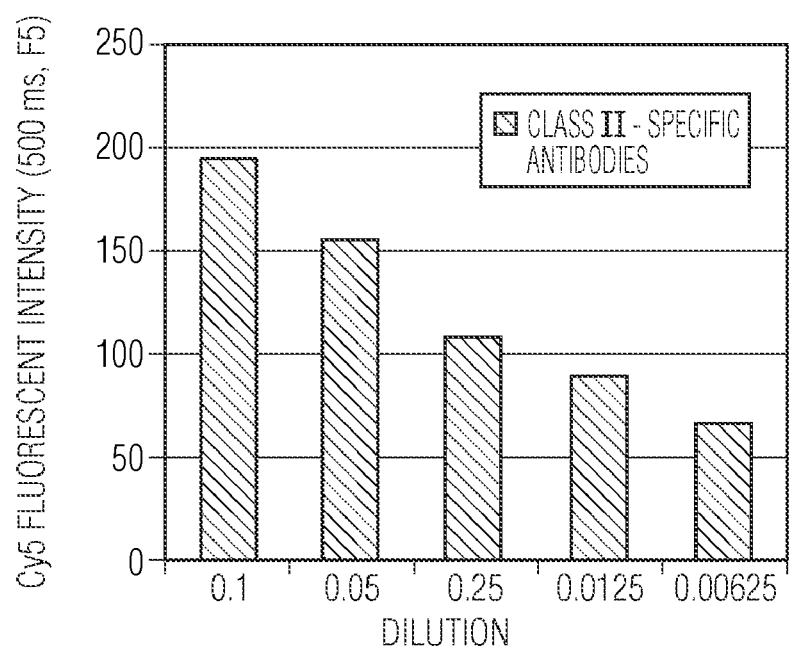

FIG. 3B depicts the class II-specific detection of HLA antigens in a spleen sample using human polyclonal serum.

Figure 4:
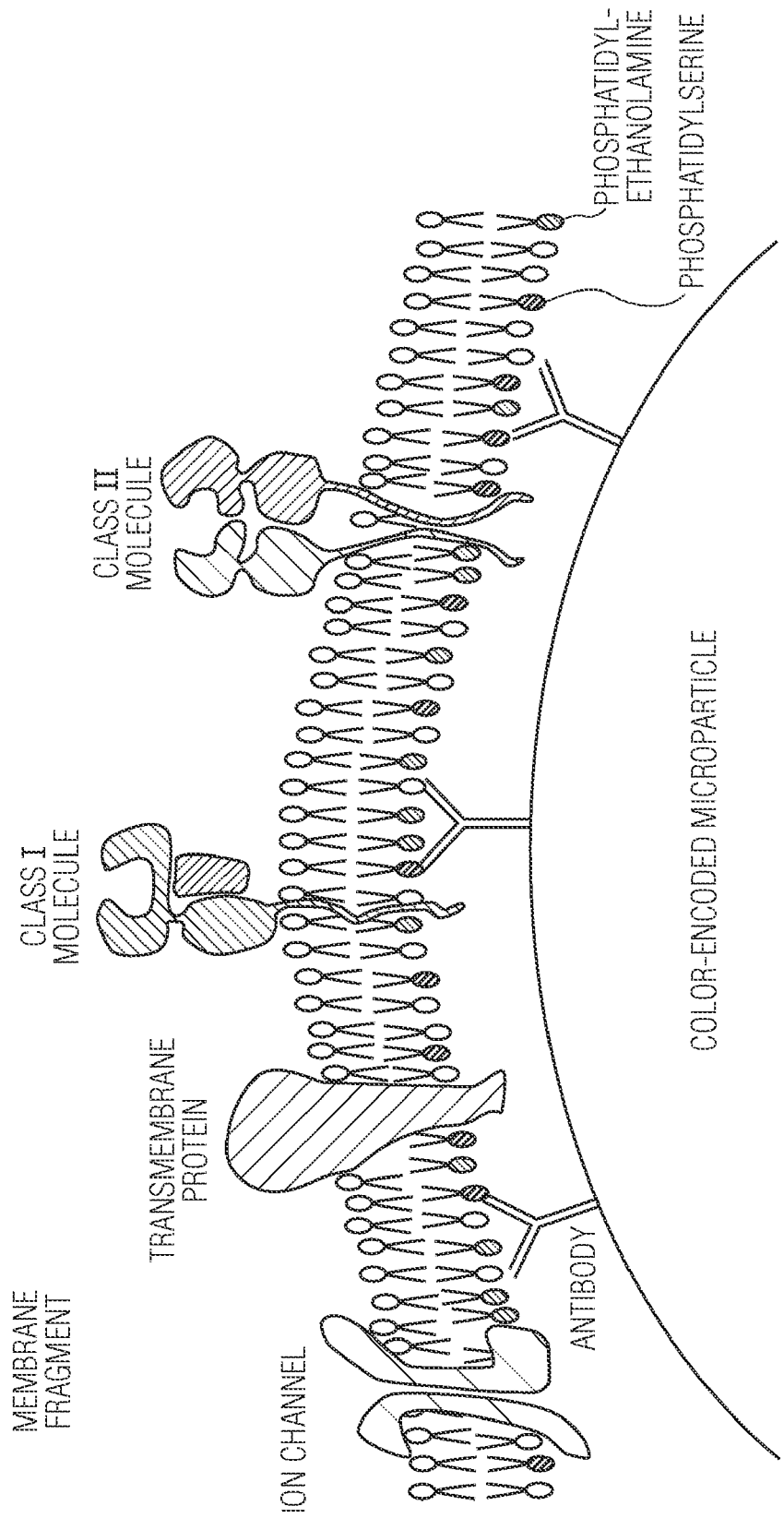

FIG. 4 depicts the configuration of a membrane fragment containing membrane-associated phospholipids displayed on a microparticle in a preferred orientation by capture to anti-phospholipid mAbs.

Figure 5A:
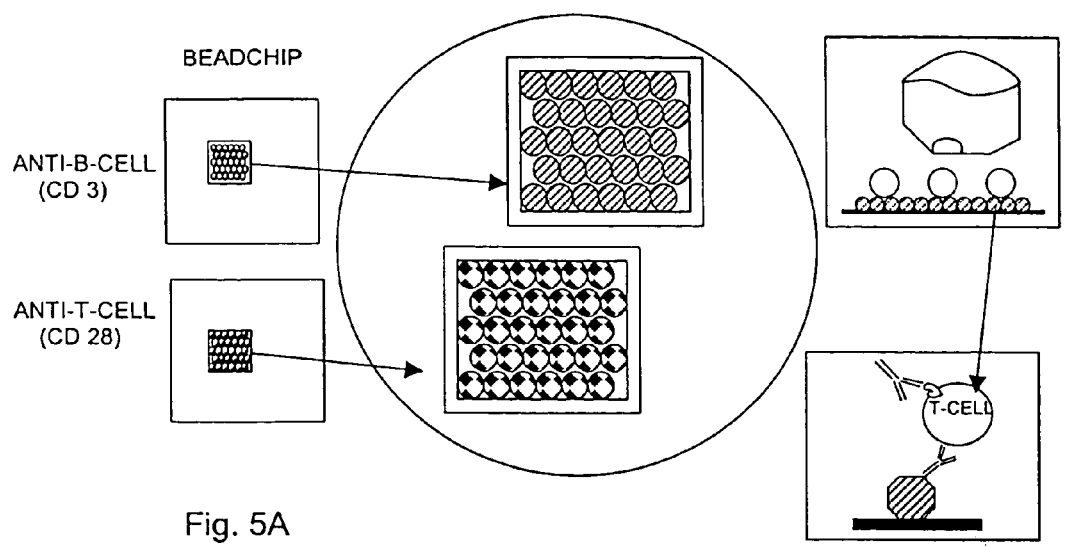

FIG. 5A depicts two arrays of beads wherein the beads in each array are coated with either a monoclonal antibody directed a B cell surface antigen or a monoclonal antibody directed against a T cell surface antigen.

Figure 5B:
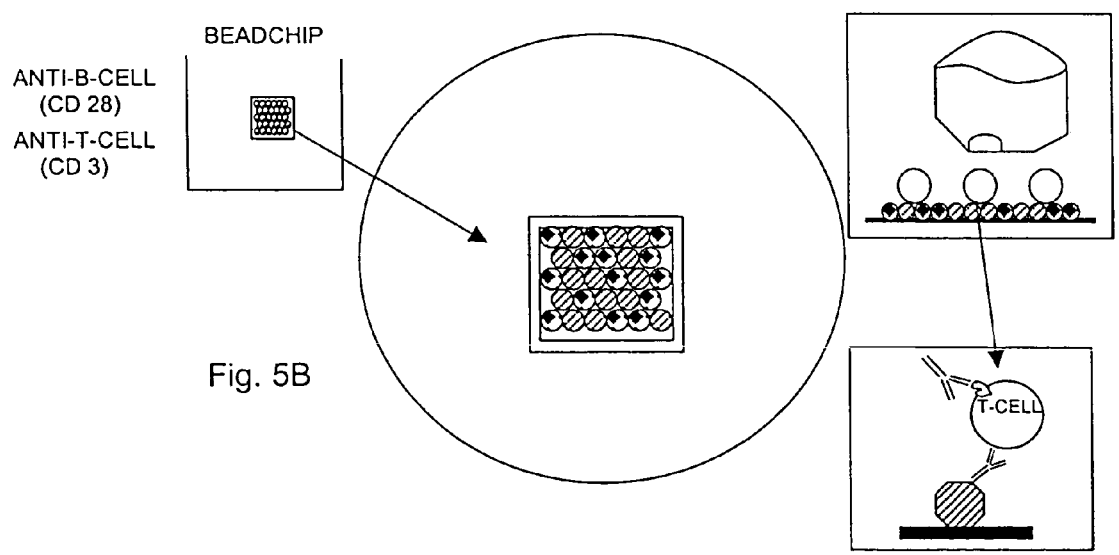

FIG. 5B depicts an array of beads wherein the beads in the array are each coated with either a monoclonal antibody directed a B cell surface antigen or a monoclonal antibody directed against a T cell surface antigen.

DETAILED DESCRIPTION

In one embodiment, each member of a set of encoded microparticles (or beads) presents HLA antigens derived from cells representative of the HLA antigens from a single human individual. Such cells may be lymphocytes, platelets or another cell population which presents HLA antigens. A preferred source is a single lymphocyte cell line or cells expressing recombinant antigens encoded by transfected HLA DNAS.

Preferably, the HLA panel is composed so as to represent the distribution of Class I and/or Class II HLA antigens in a normal human population and may also include most rare antigens; for example, native recombinant proteins. While the use of antigens from a large number of cell lines renders the panel more closely representative of the natural distribution of antigens, this desirable characteristic of such an assay design must be balanced against its rapidly increasing complexity which may reduce specificity and sensitivity.

Membrane fragments containing cell surface antigens can be affixed to encoded beads using either the method of Example I or another suitable method (see, e.g., Wilson et al., "A new microsphere-based immunofluorescence assay for antibodies to membrane-associated antigens," J. Immunol. Methods 107: 231-237 (1988)). Preferably, such fragments are oriented such that the exterior surface faces out. The lipid composition of the two layers of the lipid bilayer in cell membranes is very different. Almost all of the lipid molecules that have choline in their head group; e.g. phosphatidylcholine and sphingomyelin are in the outer leaflet of the lipid bilayer, whereas almost all of the phospholipid molecules that contain a terminal primary amino group, e.g. phosphatidylethanolamine and phosphatidylserine, are in the inner leaflet. Because the negatively charged phosphatidylserine is located in the inner monolayer, there is a significant difference in charge between the two layers of the lipid bilayer. These properties of the membrane can be exploited to orient the membrane fragment when coated on a microparticle.

The composition of the beads includes, but is not limited to, plastics, ceramics, glass, polystyrene, methylstyrene, acrylic polymers, paramagnetic materials, thoria sol, carbon graphite, titanium dioxide, latex or cross-linked dextrans such as sepharose, cellulose, nylon, cross-linked micelles and Teflon. See "Microsphere Detection Guide" from Bangs Laboratories, Fishers IN; "Method of Controlling Solute Loading of Polymer Microparticles," filed Jan. 21, 2003; U.S. Ser. No. 10/348,165, incorporated by reference. The particles need not be spherical, but may be other shapes, including conical, rod-shaped or pyramidcal, and may be porous. The bead sizes may range from nanometers (e.g., 100 nm) to millimeters (e.g., 1 mm), with beads from about 0.2 micron to about 200 microns being preferred, more preferably from about 0.5 to about 5 micron being particularly preferred. Such bead sizes can be formed into arrays suitable for viewing as a single field using a microscope, whereby the array can be decoded and analyzed. Each array may contain beads of different sizes and shapes.

Arrays of bead-displayed membrane fragments are formed in practicing the methods described herein. In one assay format, the particle-displayed ligands are assembled into an array using light-controlled electrokinetic assembly of particles, as described in U.S. Pat. Nos. 6,251,691, 6,514,771 and 6,468,811, incorporated by reference. In this method of assembly, designated LEAPS υ, the particle-displayed ligands are suspended in solution above an essentially planar electrode. If the planar electrode is modified—either by patterning or by illuminating the surface of an electrode formed, for example, by a silicon substrate—so as to form regions of reduced impedance or enhanced surface potential, an applied AC voltage on the electrode generates electric field gradients along the electrode surface in accordance with the electrode modification. Ionic movement and fluid flow transverse to the direction of the electric field then result. That is, although the electric field extends outwardly from the electrode surface, the ionic movement and fluid flow are parallel to (along) the planar electrode surface.

Particles suspended in the electrolyte solution are entrained by, and move in the direction of the electric field-induced fluid flow in accordance with their respective mobilities. In addition, once they encounter spatial modulations of impedance or surface potential in the interfacial region adjacent to the electrode, particles with a double-layer shell will respond to the corresponding local electric field gradients. Accordingly, by selectively patterning or illuminating regions of the planar electrode, one can cause particle-displayed ligands to assemble adjacent to such regions, and form arrays of bead-displayed ligands. Using LEAPS allows one to assemble relatively large bead arrays in a small region of a planar surface, which provides the advantage of having the entire array being viewable under a microscope. With a conventional cell-based assay for detecting serum or antibody reactivity, it is more diffuse and occupies a larger area, and cannot be viewed under a microscope.

Beads may be assembled using LEAPS™ or direct deposition onto a solid support. Following complex formation, the antibody-antigen complex on the surface may be detected directly according to methods known in the art including, for example, Random Encoded Array Detection (READ) (see U.S. application Ser. No. 09/690,040). This involves decoding the encoded beads to indicate the position of reactive cell fragments.

Prior to or after the formation of a bead array, the array may be immobilized prior to viewing. Following application of LEAPS to move the beads into an array, the beads can be anchored by, e.g., van der Waals forces. This anchoring process is facilitated by providing on the bead surface a population of "tethers" extending from the bead surface; polylysine and streptavidin may be used for this purpose.

In certain embodiments, the bead arrays may be immobilized by chemical means, e.g, by forming a composite gel-particle film. In one exemplary method for forming such gel-composite particle films, a suspension of beads is provided which also contains all ingredients for subsequent in situ gel formation, namely monomer, crosslinker, and initiator. The beads are assembled into a planar assembly on a substrate by application of LEAPS, e.g., AC voltages of 1-20 $V_{p-p}$ in a frequency range from 100's of hertz to several kilohertz are applied between the electrodes across the fluid gap. Following array assembly, and in the presence of the applied AC voltage, polymerization of the fluid phase is triggered by thermally heating the cell to ~40-45° C. using an infra-red (IR) lamp or photometrically using a mercury lamp source, to effectively entrap the bead array within a gel. Gels may be composed of a mixture of acrylamide and bisacrylamide of varying monomer concentrations from 20% to 5% (molar ratio, acrylamide:bisacrylamide=37.5:1), or any other low viscosity water soluble monomer or monomer mixture may be used as well. Chemically immobilized functionalized microparticle arrays prepared by this process may be used for a variety of bioassays, e.g., ligand receptor binding assays.

In certain embodiments, the bead arrays may be immobilized by mechanical means. For example, an array of microwells may be produced by standard semiconductor processing methods in the low impedance regions of the silicon substrate. The bead arrays may be formed using such structures by, e.g., utilizing LEAPS mediated hydrodynamic and ponderomotive forces are utilized to transport and accumulate beads on the hole arrays. The A.C. field is then switched off and beads are trapped into microwells and thus mechanically confined. Excess beads are removed leaving behind a geometrically ordered random bead array on the substrate surface.

The decoding image of the array and the assay image are obtained using detection means, such as a fluorescence microscope equipped with a CCD (Charge Coupled Device). The beads are decoded into specific groups or clusters and the assay signals of each group or cluster of beads are extracted and analyzed. The location of the detectably-labeled antibody-coupled beads, preferably encoded by fluorescence, is determined by analyzing the fluorescence emitted from the bead array. The amount of the antibody captured on each bead can be quantified based on signal intensity. A calibration curve of signal intensity versus concentration can be established before analysis of a sample, and this curve can be used to quantify antibody concentration in the sample by aligning the signal intensity and determining the concentration.

Image analysis algorithms may be used in analyzing the data obtained from the decoding and the assay images. These algorithms may be used to obtain quantitative data for each bead with an array. The analysis software automatically locates bead centers using a bright-field image of the array as a template, groups beads according to type, assigns quantitative intensities to individual beads, rejects "blemishes" such as those produced by "matrix" materials of irregular shape in serum samples, analyzes background intensity statistics and evaluates the background-corrected mean intensities for all bead types along with the corresponding variances. Examples of such algorithms are set forth in International Application No. PCT/US01/20179, incorporated by reference.

Other aspects and advantages of the embodiments described herein will be understood upon consideration of the following illustrative examples. An example of determining the reactivity between serum and HLAs in a sample using cell fragments coated on beads is set forth below.

EXAMPLE I

Extraction of Membrane Proteins from Lymphocytes

Membranes were extracted from human peripheral blood lymphocytes ("PBLs") and from human spleen cell preparations using the following procedure. First, the cell samples were placed in separate tubes and spun down at 14,000 g for 2 minutes. Next, the supernatant was collected and aliquots were suspended in 50 µl of 50% glycerol in 1×PBS. All the samples were frozen at −86° C. for later use.

A protease inhibitor cocktail (Signia P8340) was prepared as 100 times concentrated stock solution, and added to the following homogenization buffer, which was used to disrupt the cell membrane solution under conditions preserving their integrity. The cocktail had the formula:

250 mM sucrose
10 mM HEPES
1 mM EDTA
1 mM PMSF

Protease inhibitor cocktail (the foregoing was brought up to 10 ml with $H_2O$).

50 µl of ice cold homogenization buffer was added to the cell pellets. A mortar and pestle was used to grind the cell pellets, and the pestle was washed with 200 µl of the homogenization buffer to separate the large cell debris. The mixture was subjected to low speed centrifugation, for 10 minutes at 8000 g using a microcentrifuge at 4° C. The supernatant was extracted and added to 1/10 volume of 6.1% CHAPS, then cooled on ice for 30 minutes. The mixture was then spun down at 8000 g for 10 minutes, at 4° C., and then stored at −80° C. The pellets in each tube were resuspended in 1 ml of a PBS-CHAPS solution, consisting of:

10 µl of the 100× protease inhibitor cocktail;
100 µl of 6.1% CHAPS;
890 µl of 1× PBS (filtered).

Thereafter, the tubes were stored in ice water for 30 minutes, and spun down at 8000 g for 10 minutes at 4° C. The supernatants were saved.

The tubes were then subjected to high speed centrifugation, at 100,000 g for 30 minutes at 4° C. Following centrifugation, the pellets were resuspended in 25 µl of the PBS-CHAPS buffer and stored at −80° C.

EXAMPLE II

Determination of Relative Abundance of Class I and Class II HLA in Different Cell Lines Preparing Encoded Bead Arrays: Membrane preparations in PBS-CHAPS were extracted from different cell lines and were affixed to encoded beads of 3.2 micron diameter by placing 5 µl of a 1% suspension of such beads into each tube containing an entire preparation. Beads were collected, then resuspended in 100 µl of storage buffer containing 1% Bovine Serum Albumin with protease inhibitors. Beads coated with different membrane protein were pooled into one tube for assembly of bead arrays on chips ("Bead-Chips"). Overlapping pools of antigens are formed by including in the array membrane fragments from a sufficiently large number of cell lines so as to represent a sampling of antigens found in a normal population. Such an array permits the determination of a relative percentage of PRA simply by evaluating the percentage of bead types scoring positive in the assay.

Assay: Positive control sera reactive with HLA Class I and II antigens were placed on chips and permitted to react with the bead-displayed antisera at room temperature for two hours under gentle shaking. After incubation, the chips were washed three times with 1×PBS for three minutes at each washing.

Next, aliquots of 20 µl of Cy-5 conjugated goat anti-human IgG, or preferably the corresponding Fab fragment in 1×PBS were added to each BeadChip, and the suspension was incubated at room temperature under shaking for 1 hour. Rather than a Cy-dye (Amersham), fluorescent dyes such as Phycoerythrin (PE) or fluoresceine isothiocyanate (FITC) also can be used. Isotypes such as IgG, IgA and IgM may simultaneously be detected by employing anti-IgG, anti-IgA and/or anti-IgM antibodies labeled with a second and/or third dye, if desired. After incubation, chips were washed in lxPBS three times for three minutes each by simply exchanging aliquots of solution in contact with the BeadChips.

The BeadChips were examined using an automated Array Imaging system to record assay images showing fluorescence distribution of assay signals within the bead array and to record decoding images showing the encoding of the beads. See "ANALYSIS, SECURE ACCESS TO, AND TRANSMISSION OF ARRAY IMAGES" Ser. No. 10/714,203, filed Nov. 14, 2003; "Multianalyte Molecular Analysis Using Application-Specific Random Particle Arrays," Ser. No. 10/204,799, filed on Aug. 23, 2002, both being incorporated by reference. Fluorescence signals produced in the array labeling step indicate specific binding of allo-antibodies.

Signal thresholds to permit discrimination of positive and negative anti-HLA sera were established by analyzing positive and negative control sera. The reactivity of all bead-displayed antigens in the array was confirmed by serologically defined human alloantisera. See FIGS. 2A, 2B, 3A, 3B.

EXAMPLE III

Covalent Attachment of Proteins to Encoded Microparticles

Antibodies were covalently attached to tosyl-activated microparticles by the following method, which was used to attach anti-cytokine monoclonal antibodies to such microparticles. A similar method can be used to attach fragments, including Fab. Five hundred microlitres of PBST (Phosphate Buffered Saline (PBS), 1% vol/vol Tween-20, pH 7.2) were placed in a 1.5 mL Eppendorf tube, and fifty microliters of a suspension containing 1% w/w microparticles (0.5 mg beads) were added and mixed by vortexing. Beads were first collected by centrifuging for 3 minutes at 10,000 rpm and discarding the supernatant. Next, beads were washed once in 1 mL of PBST and once in 1 mL of PBS using centrifugation in each step as described above. Beads were resuspended in 500 μL of PBS, pH=7.2. A designated amount of specific proteins was added to each suspension at a concentration of 400 μg protein per mg beads. The coupling reaction was allowed to proceed in sealed Eppendorf tubes under slow rotation at 37° C. for 14-16 hours. Functionalized beads were collected and washed once in 500 μL of storage buffer (PBS, pH=7.2, 0.1% (w/v) IgG-free Bovine Serum Albumin (BSA), 0.1% (w/v) sodium azide), were re-suspended in 1 mL of storage buffer and were rotated for 1 hr at 37° C. This was followed by two additional wash steps (in 1 mL of storage buffer) and re-suspension in 50 μL of storage buffer maintaining a 1% solids content. Functionalized beads were stored in the dark at 4° C.

EXAMPLE IV

Random Encoded Arrays of Oriented Membrane Fragments

A. Use of Membrane Charge for Orientation. Membrane fragments can be affixed to color-encoded microparticle in a desired orientation by using particles that display positively charged chemical groups on the surface. The inner leaflet of the lipid bilayer contains negatively charged functional groups, such as, phosphatidylserine, which will be adsorbed to the positive charges of the bead surface during incubation. See FIG. 4. Particles with a negative charge or no charge can be converted into particles with a positive surface charge by conjugation with positively charged molecules according to the known art. The positively charged particles will be incubated with membrane fragments containing membrane-associated proteins of interest in a buffer containing a protease inhibitor mixture. Such membrane-associated proteins include the HLA Class I and II molecules, ion channels, GPCRs and other transmembrane proteins. Functional groups residing on the outer side, or extracellular side of the membrane, will be preferentially displayed on the particle surface in the same orientation as in the cell. Such membrane-coated particles can be used in on-chip assays for determining interactions between ligands of interest and exposed functional groups, such as class I and class II HLA, as in Example I, or membrane-associated receptors.

B. Antibody-Mediated Coupling of Membrane Fragments for Orientation The molecular composition of lipid bilayers is asymmetric. Many integral membrane proteins are distributed in the membrane in specific orientation. The carboxyl terminus of class I and II HLA molecules are located at the inner side, or cytosol side, of the membrane (FIG. 4). GPCRs, adrenergic receptors, insulin receptors, and other cell surface receptors have functional domains on the cytosol side of the membrane. Voltage-gated cation channels, such as Na+, K+, or Ca2+ are structurally related, with amino- and carboxyl-terminus as well as other functional domains located on the inner side of the membrane. In addition, most phospholipids containing a terminal amino group, such as phosphatidylserine and phosphatidylethanolamine, are located within the inner leaflet of the bilayer membrane.

Membrane fragments can be oriented in place on color-encoded microparticles by using antibodies directed specifically to molecules or epitopes of molecules located on the inner surface of the membrane. Specifically, antibodies or fragments thereof are first coupled to color-encoded microparticles according to the protocol described in Example III. Antibody-functionalized microparticles are then incubated with the membrane fragments. Specific recognition of bead-displayed molecular constituents of the cytosol leaflet of membrane fragments, will ensure that the membrane fragments will maintain the same orientation on the particles as in the cell.

EXAMPLE V

Auto-Antibody Profiling of Sera from Transplant Candidates

Using the protocol of Example III, encoded beads were covalently functionalized to display a set of auto-antigens. Random arrays of encoded functionalized eads were assembled onto silicon chips to produce BeadChips displaying a 13 auto-antigen panel for autoantibody profiling of clinical serum samples were validated using serum samples from diabetic patients. The autoantigens in this panel include centromere protein B (CENP-B), topoisomerase 1 (SCL-70), Sorgren syndrome antigen-A (SSA-52), Glutamic acid decarboxylase (GAD-65), thyroyglobulin (TG), histone, tissue transglutiminase, (t-TG), Smith antigen (Sm), Ribonuclear protein complex (Sm/RNP), Aminoacyl-tRNA synthetase (Jo-1), beta-2-glycoprotein-1, (B2-G1), myloperoxidase (MPO), and Sorgren syndrome antigen-B (La/SSB), representing polymyositosis, dennatomyositis, sclerodemia, lupus, vasculitis, colonitis, thyroditis, and type I diabetes.

The serum samples were prepared at 1:20 dilution with diluent and 10 μl of each sample were used in the subsequent assay. After incubation of 30 minutes at room temperature under shaking at 100 rpm, BeadChips were washed to remove unbound antibodies. To detect bound antibodies, BeadChips were incubated with 1:100 diluted fluorescently labeled goat anti-human IgG antibodies. After a second brief wash step, essentially just replacement of the labeling solution with wash buffer, decoding and assay images were collected and assay signals were extracted.

High anti-CENP-B, anti-TG, and anti-Jo-1 reactivity was observed in two, one, and three samples collected from diabetic patients. Weak anti-SSA-52, and anti-GAD-65 reactivity was observed in some samples.

EXAMPLE VI

Combined Auto-Antibody and Allo-Antibody Profiling

To carry out simultaneous auto-antibody and allo-antibody profiling on the same BeadChip, a random encoded bead array is assembled having both allo-antibodies affixed to particles (as in Example II) and auto-antigens on particles (as in Example V).

EXAMPLE VII

Random Encoded Array Detection Format for "Cross-Matching"

An array of encoded beads of at least two types is formed under standard conditions, encoded beads of the first type displaying a (commercially available) monoclonal antibody directed against a B-cell surface antigen such as CD 28 and the second type displaying a (commercially available) monoclonal antibody directed against a T-cell surface antigen such as CD 3. FIG. 5B. Alternatively, two separate arrays, each containing only one such bead type, also may be prepared. FIG. 5A.

The array is then incubated with serum obtained from a prospective transplant donor, and cells are allowed to interact with the bead-displayed antibodies under standard conditions permitting capture of the cells in accordance with a "panning" format. Following incubation, the donor serum is removeu, leaving only cells associated with beads displaying either anti-B cell or anti-T cell antibody. This collection of array-attached cells is readily imaged in bright-field illumination using the aforementioned Array Imaging System while bead types are readily identified under fluorescence contrast. Next, the cells are incubated with a serum sample obtained from the designated recipient under conditions permitting attachment of allo-antibodies circulating in the patient serum to cell-surface antigens on the captured cells. Following incubation, the donor serum is removed and the array-associated cells are incubated under standard conditions with a labeled secondary antibody to fluorescently decorate cell-surface captured allo-antibodies. The resulting pattern of fluorescence from the array is recorded using the aforementioned Array Imaging System, and assay signals recorded from individual cells are correlated to the decoding image revealing the encoding tag—and thereby facilitating identification—of the bead, or beads, to which cells are attached.

The terms, expressions and examples above are exemplary only and not limiting, and the scope of the invention is defined only in the claims which follow, and includes all equivalents of the subject matter of the claims. The steps of the methods set forth in the claims can be performed in any sequence, including but not limited to the sequence set forth in the claims.

What is claimed is:

1. A method for determining the presence of panel reactive antibodies in serum, said method comprising: providing a planar array of encoded microparticles of distinguishable types, wherein distinguishable types of microparticles display cell membrane fragments which originate from different cells or from different individuals and the cell membrane fragments present a known set of human leukocyte antigens (HLA) molecules; contacting said set of encoded microparticles with said serum under conditions permitting serum allo-antibodies to bind to HLA so as to form an HLA-antibody complex; removing serum and its components which do not bind to said HLA molecules; incubating, following said removal of serum, said set of microparticles with at least one labeling agent capable of binding to said HLA-antibody complexes; removing unbound labeling agent; detecting the presence of labeling agent that bound to HLA-antibody complexes on microparticles to determine the presence or absence of reactive allo-antibodies on said microparticles; decoding the labeled microparticles in order to determine the set of HLA molecules associated with said distinguishable microparticle types by correlating the position of microparticles bearing a labeling agent with microparticles bearing particular cell membrane fragments; and thereby determining the presence of microparticles in the array having reactive allo-antibodies.

2. The method of claim 1 wherein the serum is human in origin.

3. The method of claim 1 wherein the labeling agent is an antibody which specifically targets allo-antibodies.

4. The method of claim 3 wherein the labeling agent fluoresces under appropriate illumination.

5. The method of claim 3 wherein the microparticles are decoded based on correlating fluorescent labels in the array with microparticles bearing particular cell membrane fragments.

6. The method of claim 5 wherein the detection of fluorescent labels and the decoding can be accomplished using a microscope.

* * * * *